United States Patent [19]

Elliott

[11] Patent Number: 4,694,108

[45] Date of Patent: Sep. 15, 1987

[54] SYNTHESIS OF HIGHER KETONES

[75] Inventor: David J. Elliott, Bartlesville, Okla.

[73] Assignee: Phillips Petroleum Company, Bartlesville, Okla.

[21] Appl. No.: 891,838

[22] Filed: Aug. 1, 1986

[51] Int. Cl.$^4$ .............................................. C07C 45/72
[52] U.S. Cl. .................... 568/387; 568/390; 568/878; 560/232; 562/518
[58] Field of Search ................. 568/387, 390

[56] References Cited

U.S. PATENT DOCUMENTS

| | | | |
|---|---|---|---|
| 2,549,508 | 4/1951 | Mottern | 260/586 |
| 2,697,730 | 12/1954 | McCorney et al. | 260/593 |
| 2,725,400 | 11/1955 | McCorney et al. | 260/593 |
| 3,316,303 | 4/1967 | Mertzweiller et al. | 260/593 |
| 3,379,766 | 4/1968 | Hwang et al. | 260/593 |
| 3,384,668 | 5/1968 | Canter et al. | 260/593 |
| 3,496,197 | 2/1970 | Van Rheenen | 260/397.3 |
| 3,790,505 | 2/1974 | Casey et al. | 252/463 |
| 4,005,147 | 1/1977 | Fischer et al. | 568/390 |
| 4,146,581 | 3/1979 | Nissen et al. | 568/390 |
| 4,599,453 | 7/1986 | Fragale et al. | 568/387 |
| 4,599,454 | 7/1986 | Elliott et al. | 568/387 |
| 4,605,775 | 8/1986 | Elliott et al. | 568/387 |

*Primary Examiner*—James H. Reamer
*Attorney, Agent, or Firm*—K. K. Brandes

[57] ABSTRACT

A process of producing higher ketones comprises the step of contacting under suitable conditions a feed comprising (a) at least one $C_3$–$C_6$ aliphatic ketone, (b) at least one $C_2$–$C_6$ aliphatic aldehyde and, preferably, also (c) carbon monoxide with a catalyst composition comprising (i) copper or an oxide thereof and (ii) zinc oxide. Preferably, the feed ketone is methyl ethyl ketone, the feed aldehyde is propanal, and the product comprises at least one $C_7$ ketone.

29 Claims, No Drawings

SYNTHESIS OF HIGHER KETONES

BACKGROUND OF THE INVENTION

This invention relates to a catalytic process for preparing ketones. In another aspect, this invention relates to the conversion of a mixture of aldehydes and lower ketones to higher ketones.

Catalytic processes for converting lower ketones alone, or in admixture with aldehydes or alcohols, to higher ketones are known. However, there is an ever present need to develop new processes employing different catalysts and different reaction conditions so as to attain more desirable product distributions or higher yields of specific ketones.

SUMMARY OF THE INVENTION

It is an object of this invention to catalytically convert mixtures of lower ketones and aldehydes to higher ketones. It is another object of this invention to convert mixtures of lower ketones and aldehydes to higher ketones having at least one carbon atom per molecule more than said lower ketones. It is a further object of this invention to convert a mixture of methyl ethyl ketone (butanone) and propionaldehyde (propanal) to at least one ketone having at least 7 carbon atoms per molecule. Other objects and advantages will be apparent from the detailed description and the apended claims.

In accordance with this invention, a feed comprising (a) at least one aliphatic ketone having from 3 to 6 carbon atoms per molecule (preferably butanone) and (b) at least one aliphatic aldehyde having from 2 to 6 carbon atoms per molecule (preferably propanal) is contacted with a catalyst composition comprising (i) at least one of copper and copper oxide and (ii) zinc oxide, under such contacting conditions (preferably in the substantial absence of free hydrogen in the feed) as to obtain a product comprising at least one higher ketone having at least one carbon atom per molecule more than the ketone in said feed. Preferably said higher ketone has at least 7 carbon atoms per molecule, and more preferably is a heptanone.

In a preferred embodiment, the feed additionally comprises (c) carbon monoxide. In another preferred embodiment, the feed consists essentially of components (a), (b) and (c) as defined above.

In still another preferred embodiment, the catalyst composition in the process of this invention comprises (i) at least one of copper and copper oxide, (ii) zinc oxide and (iii) an inorganic refractory oxide support material (preferably alumina). In a further preferred embodiment, the catalyst composition comprising CuO and ZnO is pretreated by heating with a reducing gas (such as CO and/or $H_2$), preferably a free hydrogen containing gas, under such conditions as to at least partially reduce CuO to $Cu_2O$ and/or Cu metal, before the catalyst composition is used in the process of this invention. In a still further preferred embodiment the catalyst composition consists essentially of components (i), (ii) and (iii) as defined above.

DETAILED DESCRIPTION OF THE INVENTION

The catalyst composition employed in the process of this invention comprises (i) oxide of copper and/or copper metal and (ii) zinc oxide. Preferably the mixed oxide of Cu and Zu is prepared by coprecipitation of either the hydroxides of copper and zinc and/or the carbonates of copper and zinc, e.g. by addition of a base such as NaOH, or a soluble carbonate such as $Na_2CO_3$, to an aqueous solution of copper and zinc salts such as nitrates, halides or sulfates of copper and zinc, and subsequent calcination (heating in air) under such conditions as to form the oxides of copper and zinc.

In a preferred embodiment, an inorganic refractory oxide support material such as alumina, silica, aluminosilicate, titania, zirconia, magnesia, alumina phosphate, zirconium phosphate, mixtures of the above and the like, preferably alumina, is also present in said catalyst composition. More preferably the catalyst composition is prepared by either coprecipitation of hydroxides and/or carbonates of copper, zinc and aluminum and subsequent calcination under such conditions as to form the oxides of copper, zinc and aluminum; or by coprecipitation of hydroxides and/or carbonates of copper and zinc from an aqueous solution containing dispersed alumina, and subsequent calcination; or by the method described in U.S. Pat. No. 3,790,505, herein incorporated by reference. CuO-ZnO containing catalyst compositions are commercially available from United Catalysts, Inc., Louisville, Ky. and from BASF Wyandotte Corporation, Parsippany, N.J.

In a preferred embodiment, a CuO-ZnO containing catalyst composition used in the process of this invention is pretreated by heating with a reducing gas (e.g., $H_2$, CO), preferably a free hydrogen containing gas, so as to partially reduce CuO to $Cu_2O$ and/or Cu metal, before the catalyst composition is employed in the process of this invention. More preferably, said heating is carried out with a free hydrogen containing gas, most preferably a $H_2/N_2$ mixture containing 2-5 volume-% $H_2$, at about 350°–450° F. for about 1-6 hours.

Preferably the weight ratio of Cu (present as metal or oxide) to Zn (present as oxide) in the catalyst composition ranges from about 1:20 to about 20:1, more preferably from about 1:3 to about 3:1. If alumina ($Al_2O_3$) or (less preferably) another inert refractory material as defined above is also present in said catalyst composition, the weight percentage of said inert material (preferably alumina) in the catalyst composition can range from about 1 to about 90 weight-%, preferably from about 10 to about 70 weight-%. Generally the surface area (determined by the BET/$N_2$ method, ASTM D3037) of the catalyst composition ranges from about 20 $m^2$/g to about 300 $m^2$/g, preferably from about 50 $m^2$/g to about 200 $m^2$/g.

The feed that is contacted with the CuO-ZnO containing catalyst composition comprises (a) at least one aliphatic ketone having from 3 to 6 carbon atoms per molecule and (b) at least one aliphatic aldehyde having from 2 to 6 carbon atoms per molecule. The volume ratio of the ketone to the aldehyde in the feed generally ranges from about 1:100 to about 100:1, preferably from about 1:20 to about 20:1, measured at about 550° F. and 15 psia. An inert gas such as nitrogen or helium can also be present in said feed stream. The use of hydrogen gas and of water vapor as components of the feed mixture is presently not contemplated in the process of this invention.

Non-limiting examples of suitable lower feed ketones are acetone, methyl ethyl ketone, diethyl ketone, methyl propyl ketone, ethyl propyl ketone, methyl isobutyl ketone, and mixtures thereof. Non-limiting examples of feed aldehydes are acetaldehyde, propanal (propionaldehyde), n-butanal, isobutanal, straight-chain pentanals, branched pentanals, straight-chain hexanals, branched hexanals, and mixtures thereof. Preferred feed compounds are butanone (methyl ethyl ketone) and propanal (propionaldehyde).

In a preferred embodiment, the feed also contains carbon monoxide. The presence of CO in the feed results in higher conversion of lower ketone and aldehyde and in enhanced selectivity to higher ketones in the formed product. Preferably, the volume ratio of lower ketone vapor to carbon monoxide generally is in the range of from about 1:100 to about 20:1, preferably from about 1:20 to about 1:1, measured at about 550° F. and 15 psia (1 atm).

The ketone and aldehyde containing feed can be contacted with the catalyst composition in any suitable manner. A stream containing a vaporized ketone having from 3 to 6 carbons, a stream containing a vaporized aldehyde having from 2 to 6 carbon atoms and, preferably, also a carbon monoxide containing stream can be passed separately into a suitable reaction vessel, and can then be contacted in at least partially mixed form with the catalyst composition under suitable reaction conditions. The ketone and aldehyde containing feed streams can be introduced as substantially liquid streams, which will then vaporize in the reactor, or they can be introduced as substantially vaporized streams. Or the feed streams can be premixed and then be contacted with the catalyst composition under suitable reaction conditions so as to produce a reaction product comprising at least one ketone containing at least 1 carbon atom per molecule more than the feed ketone.

The process of this invention can be carried out as a batch process or as a continuous process. In a batch process, the process ingredients are charged in any order to a vessel equipped with pressuring and heating means, and the ingredients are then kept in contact with the catalyst composition for a certain length of time under suitable reaction conditions so as to produce a product comprising at least one ketone containing at least 1 C atom per molecule more than the feed ketone. In this type of operation, the catalyst can be dispersed in the feed stream (generally gaseous) as a fluidized bed; or the feed stream can be circulated through a fixed bed containing the catalyst composition. In a continuous process, which is presently preferred, the feed streams can be passed, at least partially mixed, through a fixed bed containing the solid catalyst composition, under such conditions as will result in a product comprising at least one ketone containing at least 1 C atom per molecule more than the feed ketone. Optionally, an inert gas can be present during the batch or continuous process.

Heating of the process ingredients is generally required to accomplish at least partial conversion of feed ketone and aldehyde to at lease one ketone containing at least one additional carbon atom per molecule than the feed ketone. Any suitable temperature that will cause and maintain a controllable reaction can be employed. Any feasible heating means can be utilized. It is within the scope of this invention to preheat one or more of the process ingredients before they are introduced into a reactor, which is heated to maintain a suitable temperature. The reaction temperature generally ranges from about 200° C. to about 400° C., preferably from about 250° C. to about 300° C.

The reaction pressure generally is above atmospheric pressure. The selection of the reaction pressure will greatly depend on the reaction temperature, the feed rates of feed and the specific reactor design. Generally the pressure ranges from about 1 psig to about 5,000 psig, preferably about 200 psig to about 2,000 psig.

The reaction time, i.e., the time of intimate, simultaneous contact of all process ingredients, can vary from 0.01 to about 60 minutes and will preferably be in the range of about 0.1 to about 10 minutes. The actual reaction time will greatly depend on the flow rates of feed ketone, aldehyde and, optionally (preferably), carbon monoxide, on the selection of an effective, yet safe reaction temperature, on the extent of mixing and agitation (if any) during the reaction, and on the amount of the catalyst employed. In a continuous process, the gas hourly space velocity of the combined feed stream comprising lower ketone, aldehyde and, optionally, CO ranges generally from about 100 to about 10,000 cc feed stream/cc catalyst/hour, preferably from about 1,000 to about 5,000 cc/cc/hr, measured at about 550° F. and 15 psia.

The formed reaction product which comprises at least one ketone containing at least one C atom per molecule more than the feed ketone can be separated from the reaction mixture by any suitable separation means such as condensation, crystallization, absorption, fractional distillation, or extraction with a suitable solvent plus subsequent evaporation of the solvent. Unreacted process ingredients can be at least partially separated in a similar manner and can be recycled to the reaction zone where the conversion of lower ketones and aldehydes to higher ketones in accordance with this invention occurs.

If a reaction product containing more than one ketone and esters is formed, said product can be separated into the pure components by any of the above-cited or other known separation means. Compositions of products formed from the preferred ketone, methyl ethyl ketone, and the preferred aldehyde, propanol, under specific reaction conditions are presented in the Examples. Ketones prepared by the process of this invention can be used as solvents and/or as reactants in various organic synthesis.

The following examples are presented to further illustrate this invention without unduly limiting the scope of the invention.

EXAMPLE I

This example illustrates the conversion of methyl ethyl ketone and to higher ketones, particularly heptanones, in the presence of a 16/40 mesh $CuO$-$ZnO$-$Al_2O_3$ catalyst which was prepared substantially in accordance with the procedure of Example I of U.S. Pat. No. 3,790,505, herein incorporated y reference. The catalyst contained about 30 weight-% $CuO$, about 31 weight-% $ZnO$ and about 39 weight-% $Al_2O_3$, and had a BET/$N_2$ surface area of about 42 $m^2/g$. The reactor used was a vertical, tubular, stainless steel reactor having an inner diameter of about one-half inch and a catalyst bed length of about 5-6 inches, and was heated by means of an outside furnace. The reactor was filled as follows: top layer of 5 cc 16 mesh Alundum (having a surface area of less than 1 $m^2/g$; marketed by Norton Chemical Process Products, Akron, Ohio); middle layer of 2.5 cc (3.0 g) of the $CuO$-$ZnO$-$Al_2O_3$ catalyst plus 7.5 cc 16 mesh Alundum; bottom layer of 5 cc 16 mesh Alundum. A thermocouple was axially inserted into the catalyst bed.

First, the catalyst bed in the reactor was pretreated with a $H_2/N_2$ gas mixture (having $H_2:N_2$ volume ratio of 3:97) at about 390°–400° F., for a time period of about 4 hours. Then the reactor was purged with nitrogen, the temperature was raised to 540°–550° F., and the required feed streams were charged to the reactor.

In control run 1, liquid methyl ethyl ketone (butanone) was charged at a rate of 1.5–2.3 cc/hr, and nitrogen gas was charged at a rate of 140 cc/min to the reactor so as to provide a combined gas stream containing about 90 volume-% $N_2$. In invention run 2, the feed rates of methyl ethyl ketone and of $N_2$ were substantially the same as in run 1, but additionally liquid propanal (propionaldehyde) was charged at a rate of about 2.3 cc/hr. In both runs, the feed streams were substantially free of water and hydrogen gas.

The product stream was cooled by a cold trap having a temperature of about 30° F., so as to condense the less volatile components. The off-gas product stream was analyzed by means of a modified Applied Automation Model 12 gas chromatograph (GC), whereas the liquid product was analyzed by means of a Hewlett-Packard Model 5750 gas chromatograph with a methyl silicone lined capillary column. The various components of the liquid product separated by GC were confirmed by mass spectrometry. Results are summarized in Table I.

TABLE I

|  | Run 1 (Control) | Run 2 (Invention) |
|---|---|---|
| Ketone Feed | Butanone | Butanone |
| Aldehyde Feed | None | Propanal |
| Gas Feed | $N_2$ | $N_2$ |
| % Conversion of Butanone | 5.6 | 21 |
| % Conversion of Propanal | — | 85 |
| Composition of Liquid Product: |  |  |
| Wt % of 1-Propanol | — | 1.5 |
| Wt % of Propanal | — | 8.0 |
| Wt % of Propionic Acid | — | 6.0 |
| Wt % of $C_4$ Hydrocarbons | — | 0.1 |
| Wt % of 2-Butanol | — | 0.5 |
| Wt % of Butanone | 94.3 | 42.9 |
| Wt % of $C_5$ Alcohols | 0.3 | — |
| Wt % of $C_5$ Ketones | — | 1.8 |
| Wt % of $C_6$ Alcohols | 1.0 | — |
| Wt % of $C_6$ Aldehydes | — | 5.5 |
| Wt % of Propyl Propionate | — | 16.5 |
| Wt % of $C_6$ Ketones | 0.5 | 1.1 |
| Wt % of 3-Heptanone | 0.9 | 9.2 |
| Wt % of Olefinic $C_7$ Ketones | — | 2.9 |
| Wt % of $C_7$ Alcohols and Esters[1] | 0.8 | 3.1 |
| Wt % of $C_8$ Ketones | 1.2 | — |
| Wt % of Others | 1.2 | 1.0 |

[1] unidentified.

Data in Table I demonstrate that the presence of propanal in the feed significantly enhanced the conversion of butanone (methyl ethyl ketone) and the yield of $C_7$ ketones. The formation of $C_8$ ketones was not observed in invention run 2, and thus essentially no dimerization of butanone occurred when propanal was present as a co-feed. A sizable amount of propyl propionate was also formed, most probably by dimerization of propanal.

Analysis of the gas product formed in run 2 revealed that about 99 volume-% was nitrogen, about 0.2 volume-% was hydrogen, and about 0.2 volume-% was carbon dioxide. The remainder comprised mainly hydrocarbons and unreacted propanal.

EXAMPLE II

This example illustrates the conversion of butanone and propanal to primarily $C_5$–$C_7$ ketones in the presence of carbon monoxide as co-feed (instead of nitrogen as described in Example I). The feed rate of CO in invention run 3 was the same as that of $N_2$ in run 2. The experimental procedure was essentially the same as that described for run 2 in Example I, except that CO was used in lieu of $N_2$. Again, water and hydrogen gas were substantially absent in all feed streams. Pertinent test data are summarized in Table II.

TABLE II

|  | Run 2 (Invention) | Run 3 (Invention) | Run 4 (Control) |
|---|---|---|---|
| Ketone Feed | Butanone | Butanone | Butanone |
| Aldehyde Feed | Propanal | Propanal | None |
| Gas Feed | $N_2$ | CO | CO |
| % Conversion of Butanone | 21 | 54 | 41 |
| % Conversion of Propanal | 85 | 97 | — |
| Composition of Liquid Products: |  |  |  |
| Wt % of 1-Propanol | 1.5 | 0.6 | — |
| Wt % of Propanal | 8.0 | 1.4 | — |
| Wt % of Propionic Acid | 6.0 | — | — |
| Wt % of $C_4$ Hydrocarbons | 0.1 | 0.3 | 0.4 |
| Wt % of 2-Butanol | 0.5 | 1.4 | — |
| Wt % of Butanone | 42.5 | 30.7 | 63.1 |
| Wt % of $C_5$ Ketones | 1.8 | 8.2[1] | 0.6 |
| Wt % of $C_6$ Alcohols | — | 0.2 | — |
| Wt % of $C_6$ Aldehydes | 5.5 | — | — |
| Wt % of Propyl Propionate | 16.5 | 9.0 | — |
| Wt % of $C_6$ Ketones | 1.1 | 10.2[2] | 3.6 |
| Wt % of 3-Heptanone | 9.2 | 18.9 | 1.3 |
| Wt % of Other $C_7$ Ketones | 2.9 | 4.5 | — |
| Wt % of $C_7$ Alcohols and Esters[3] | 3.1 | 0.6 | — |
| Wt % of $C_8$ Ketones | — | 3.6 | 26.8 |
| Wt % of Others | 2.8 | 10.3 | 4.3 |

[1] Mainly 3-pentanone; some 3-methyl-2-butanone
[2] Mainly 2-methyl-3-pentanone; some 3-hexanone
[3] Unidentified esters Data in Table II clearly show that the conversion of both butanone and propanal was significantly increased when CO was present in the feed (compare runs 2 and 3). Furthermore, the presence of CO caused a significant increase in the production of $C_5$ ketones, $C_6$ ketones and $C_7$ ketones (compare runs 2 and 3). When propanal was left out as a feed component, lower butanone conversion, lower yields of $C_5$–$C_7$ ketones and higher yield of $C_8$ ketones (probably formed by dimerization of butanone) resulted (compare runs 3 and 4).

Analysis of the gas product formed in run 3 revealed that about 95 volume-% was carbon monoxide, about 3.2 volume-% was carbon dioxide, and the remainder comprised $C_2$–$C_5$ hydrocarbons.

Reasonable variations and modifications are possible within the scope of the disclosure and the appended claims.

I claim:

1. A process for preparing higher ketones comprising the step of contacting a feed comprising
   (a) at least one aliphatic ketone having from 3 to 6 carbon atoms per molecule and
   (b) at least one aliphatic aldehyde having from 2 to 6 carbon atoms per molecule with a catalyst composition comprising
      (i) at least one of copper and copper oxide and
      (ii) zinc oxide, in the substantial absence of free hydrogen in said feed, under such contacting conditions as to obtain a product comprising at least one ketone having at least one carbon atom per molecule more than said aliphatic ketone (a).

2. A process in accordance with claim 1, wherein said catalyst composition additionally comprises (iii) inorganic refractory oxide support material.

3. A process in accordance with claim 2, wherein catalyst component (iii) is alumina.

4. A process in accordance with claim 1, wherein said aliphatic ketone (a) is methyl ethyl ketone and said aliphatic aldehyde (b) is propanal.

5. A process in accordance with claim 1, wherein said product comprises at least one ketone having at least 7 carbon atoms per molecule.

6. A process in accordance with claim 1, wherein the volume ratio, measured at about 550° F. and 15 psia, of aliphatic ketone (a) to aliphatic aldehyde (b) is in the range of from about 1:100 to about 100:1.

7. A process in accordance with claim 6, wherein said volume ratio is in the range of from about 1:20 to about 20:1.

8. A process in accordance with claim 1, wherein the weight ratio of Cu to Zn in said catalyst composition is in the range of from aobut 1:20 to about 20:1.

9. A process in accordance with claim 8, wherein said weight ratio of Cu to Zn is in the range of from about 1:30 to about 3:1.

10. A process in accordance with claim 1, wherein said catalyst composition comprises alumina and the weight percentage of alumina in said catalyst composition is in the range of from about 1 to about 90 weight-%.

11. A process in accordance with claim 10, wherein said weight percentage of alumina is in the range of from about 10 to about 70 weight-%, and the surface area of said catalyst composition is in the range of from about 20 to about 300 m$^2$/g.

12. A process in accordance with claim 1, wherein said catalyst has been pretreated with a reducing gas under such conditions as to at least partially reduce CuO, which is present in said catalyst composition, to at least one of Cu$_2$O and Cu.

13. A process in accordance with claim 1, wherein said contacting conditions comprise a reaction temperature in the range of from about 200° to about 400° C., a reaction pressure in the range of from about 1 to about 5,000 psig, and a reaction time in the range of from about 0.01 to about 60 minutes.

14. A process in accordance with claim 13, wherein said reaction temperature is in the range of from about 250° to about 300° C. and said reaction pressure is in the range of from about 200 to about 2000 psig.

15. A process for preparing higher ketones comprising the step of contacting a feed comprising
(a) at least one aliphatic ketone having from 3 to 6 carbon atoms per molecule,
(b) at least one aliphatic aldehyde having from 2 to 6 carbon atoms per molecule, and
(c) carbon monoxide with a catalyst composition comprising
  (i) at least one of copper and copper oxide and
  (ii) zinc oxide, under such contacting conditions as to obtain a product comprising at least one ketone having at least one carbon atom per molecule more than said aliphatic ketone (a).

16. A process in accordance with claim 15, wherein said catalyst composition additionally comprises (iii) inorganic refractory oxide support material.

17. A process in accordance with claim 16, wherein catalyst component (iii) is alumina.

18. A process in accordance with claim 15, wherein said aliphatic ketone (a) is methyl ethyl ketone and said aliphatic aldehyde (b) is propanal.

19. A process in accordance with claim 15, wherein said product comprises at least one ketone having at least 7 carbon atoms per molecule.

20. A process in accordance with claim 15, wherein the volume ratio of aliphatic ketone (a) to aliphatic aldehyde (b) is in the range of from about 1:100 to about 100:1, and the volume ratio of aliphatic ketone (a) to carbon monoxide is in the range of from about 1:100 to about 2:1, both volume ratios being measured at about 550° F. and 15 psia.

21. A process in accordance with claim 20, wherein said volume ratio of aliphatic ketone (a) to aliphatic aldehyde (b) is in the range of from about 1:20 to about 20:1, and said volume ratio of aliphatic ketone (a) to carbon monoxide is in the range of from about 1:20 to about 1:1.

22. A process in accordance with claim 15, wherein the weight ratio of Cu to Zn in said catalyst composition is in the range of from aobut 1:20 to about 20:1.

23. A process in accordance with claim 22, wherein said weight ratio of Cu to Zn is in the range of from about 1:30 to about 3:1.

24. A process in accordance with claim 15, wherein said catalyst composition comprises alumina and the weight percentage of alumina in said catalyst composition is in the range of from about 1 to about 90 weight-%.

25. A process in accordance with claim 24, wherein said weight percentage of alumina is in the range of from about 10 to about 70 weight-%, and the surface area of said catalyst composition is in the range of from about 20 to about 300 m$^2$/g.

26. A process in accordance with claim 15, wherein said catalyst has been pretreated with a reducing gas under such conditions as to at least partially reduce CuO, which is present in said catalyst composition, to at least one of Cu$_2$O and Cu.

27. A process in accordance with claim 15, wherein said contacting conditions comprise a reaction temperature in the range of from about 200° to about 400° C., a reaction pressure in the range of from about 1 to about 5,000 psig, and a reaction time in the range of from about 0.01 to about 60 minutes.

28. A process in accordance with claim 27, whrein said reaction temperature is in the range of from about 250° to about 300° C., and said reaction pressure is in the range of from about 200 to about 2000 psig.

29. A process in accordance with claim 15, wherein said contacting is carried out in the substantial absence of free hydrogen and water vapor in said feed.

* * * * *